United States Patent
Merz et al.

(10) Patent No.: US 9,034,637 B2
(45) Date of Patent: May 19, 2015

(54) APPARATUS AND METHOD FOR MOLECULE DETECTION USING NANOPORES

(75) Inventors: Matthias Merz, Leuven (BE); Youri V. Ponomarev, Leuven (BE); Gilberto Curatola, Korbek-Lo (BE)

(73) Assignee: NXP, B.V., Eindhoven (NL)

(*) Notice: Subject to any disclaimer, the term of this patent is extended or adjusted under 35 U.S.C. 154(b) by 1193 days.

(21) Appl. No.: 12/595,090

(22) PCT Filed: Apr. 5, 2008

(86) PCT No.: PCT/IB2008/051438
§ 371 (c)(1),
(2), (4) Date: Oct. 8, 2009

(87) PCT Pub. No.: WO2008/132643
PCT Pub. Date: Nov. 6, 2008

(65) Prior Publication Data
US 2010/0066348 A1 Mar. 18, 2010

(30) Foreign Application Priority Data
Apr. 25, 2007 (EP) .................................. 07106908

(51) Int. Cl.
| | | |
|---|---|---|
| C12M 1/34 | (2006.01) | |
| C12M 1/00 | (2006.01) | |
| C12M 3/00 | (2006.01) | |
| G01R 31/26 | (2014.01) | |
| H01L 21/66 | (2006.01) | |
| G01N 33/487 | (2006.01) | |
| C12Q 1/68 | (2006.01) | |
| G01N 27/414 | (2006.01) | |

(52) U.S. Cl.
CPC ........ *G01N 33/48721* (2013.01); *C12Q 1/6869* (2013.01); *G01N 27/414* (2013.01)

(58) Field of Classification Search
None
See application file for complete search history.

(56) References Cited

U.S. PATENT DOCUMENTS 5,013,681 A * 5/1991 Godbey et al. ................ 438/459
5,357,119 A * 10/1994 Wang et al. .................... 257/18
(Continued)

FOREIGN PATENT DOCUMENTS

| EP | 1433744 A1 | 6/2004 |
|---|---|---|
| EP | 1486775 A1 | 12/2004 |

(Continued)

OTHER PUBLICATIONS

Hu et al, Applied Physics Letters, vol. 71, pp. 2020-2022, Oct. 6, 1997.*

(Continued)

*Primary Examiner* — Robert T Crow

(57) ABSTRACT

A detector device comprises a substrate (50), a source region (S) and a drain region (D), and a channel region (65) between the source and drain regions. A nanopore (54) passes through the channel region, and connects fluid chambers (56,58) on opposite sides of the substrate. A voltage bias is provided between the fluid chambers, the source and drain regions and a charge flow between the source and drain regions is sensed. The device uses a nanopore for the confinement of a sample under test (for example nucleotides) close to a sensor. The size of the sensor can be made similar to the spacing of adjacent nucleotides in a DNA strand. In this way, the disadvantages of PCR based techniques for DNA sequencing are avoided, and single nucleotide resolution can be attained.

28 Claims, 7 Drawing Sheets

(56) References Cited

U.S. PATENT DOCUMENTS

| | | | |
|---|---|---|---|
| 5,993,611 A * | 11/1999 | Moroney et al. | 204/157.6 |
| 2003/0003609 A1 * | 1/2003 | Sauer et al. | 438/14 |
| 2003/0104428 A1 | 6/2003 | Branton et al. | |
| 2003/0231531 A1 | 12/2003 | Baxter et al. | |
| 2005/0102721 A1 | 5/2005 | Barth | |
| 2005/0227239 A1 * | 10/2005 | Joyce | 435/6 |
| 2006/0052947 A1 * | 3/2006 | Hu | 702/20 |
| 2006/0086626 A1 * | 4/2006 | Joyce | 205/792 |
| 2006/0275778 A1 | 12/2006 | Wu et al. | |
| 2007/0178507 A1 | 8/2007 | Wu et al. | |

FOREIGN PATENT DOCUMENTS

| | | |
|---|---|---|
| EP | 1657539 A1 | 5/2006 |
| GB | 2416210 A | 1/2006 |
| WO | 01/81896 A | 11/2001 |
| WO | 2005015193 A1 | 2/2005 |

OTHER PUBLICATIONS

The defintion of "circuit" provided by the online dictionary at thefreedictionary.com ([retrieved on Jul. 31, 2012]; retrieved from the Internet: <URL: www.thefreedictionary.com/circuit>.*

The difinition of "bias" provided by the online dictionary at dictionary.com ([retrieved on Jul. 31, 2012]; retrieved from the Internet: <URL: www.dictionary.com/browse/bias>.*

Mali, R. K., et al; "The DNA Set: A Novel Device for Single-Molecule DNA Sequencing": IEEE Transactions on Electron Devices; IEEE Service Center, Pisacataway, NJ, US; vol. 51, No. 12; Dec. 1, 2004; pp. 2004-2012; XP011122900; ISSN: 0018-9383.

Current, M.I., et al; "What is the Future of Sub-100nm CMOS: Ultrashallow Junctions or Ultrathin SOI?"; Solid State Technology; Pennwell Corporation; Tulsa, OK, US; vol. 43, No. 9; Sep. 1, 2000; pp. 66-68; XP000969250; ISSN: 0038-111X.

Branton, Daniel; "Nanopore Tranducers: Prospectis for Single Molecule Electrophresis"; Harvard University; Cambridge, MA, US; 12 Int'l Conference on Solid State Sensors, Actuators and Microsystems, Boston, MA, US, Jun. 8-12, 2003.

Jacquot, Blake C. et al; "Electrolyte Pulse Current Measurements by CvMOS with Microsecond and Thermal Voltage Resolution"; 28th Intl. Conf. IEEE Engineering in Medicine and Biology Society, Aug. 30-Sep. 3, 2006, New York, New York, US; 4 pages (Sep. 2006).

Lagerqvist, J. et al; "Fast DNA sequencing via transverse electronic transport"; Nano Lett 6 (4); pp. 779-782 (Apr. 2006).

Zikic, R. et al.: :Characterization of the tunneling conductance across DNA bases; Physical Review E 74 (1): Art. No. 011919 Part 1 (Jul. 2006).

Meirav, U. et al; "Single-electron phenomena in semiconductors"; Semiconductor Science and Technology 11 (3); pp. 255-284 (Mar. 1996).

Smith, C.G.; "Low-dimensional quantum devices"; Reports on Progress in Physics 59 (2); pp. 235-282 (Feb. 1996).

Wesolowski, Steven S. et al, Electron Affinities of the DNA and RNA Bases; J. Am. Chem. Soc., vol. 123, No. 17; pp. 4023-4028 (2001).

* cited by examiner

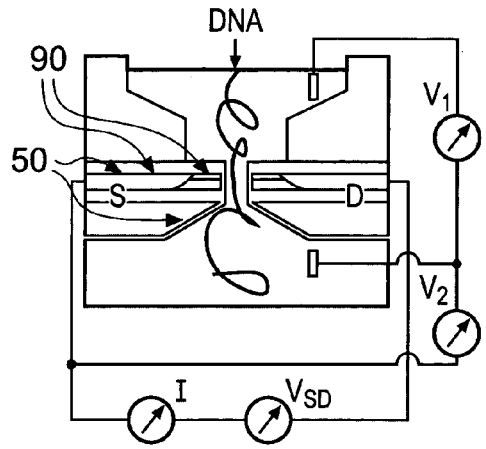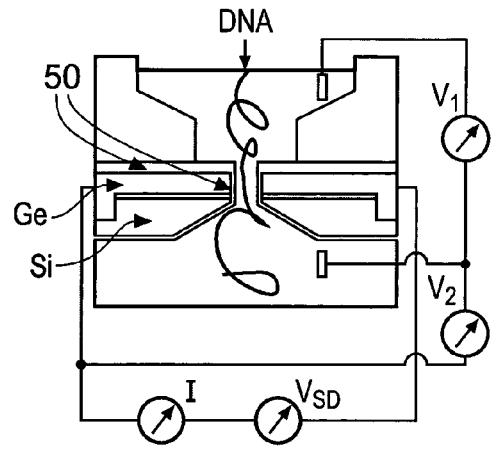
FIG. 7a  FIG. 7b
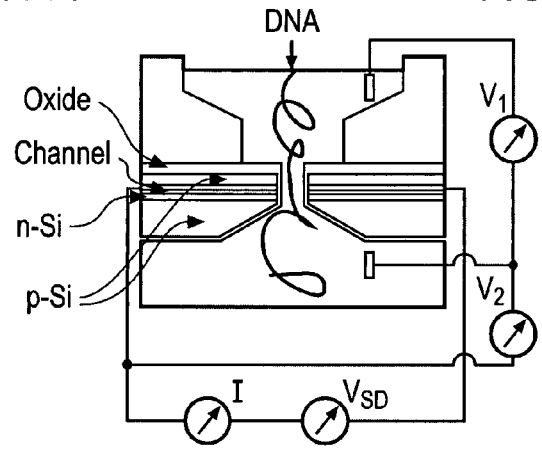
FIG. 7c
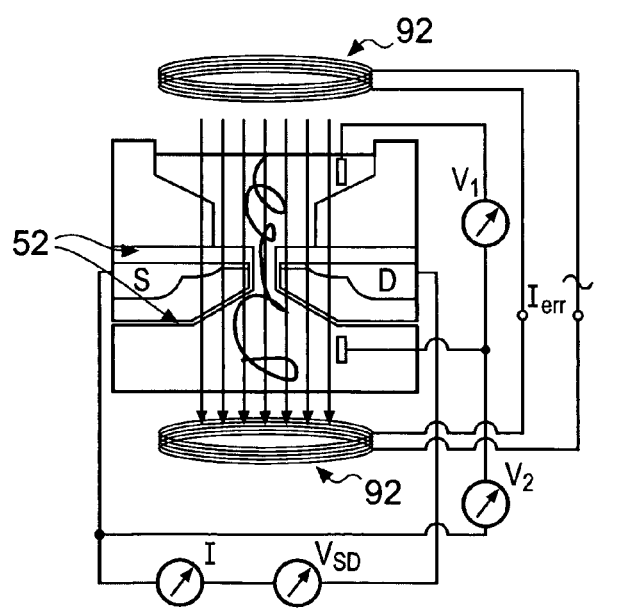
FIG. 7d

APPARATUS AND METHOD FOR MOLECULE DETECTION USING NANOPORES

This invention relates to apparatus and methods for detection of molecules, for example polymer molecules. The invention relates specifically to nanopore molecule detectors, for example for use in detecting DNA nucleotide monomers.

DNA is a double helix consisting of two strands of molecules. Each strand is formed as a chain of the four nucleotides adenine (A), thymine (T), cytosine (C) and guanine (G). The order or sequence of these nucleotides encodes all information for metabolism and reproduction in any living organism. In humans each DNA strand consists of more than 3 Billion nucleotides.

Knowing the DNA sequence of a species is interesting from a basic research point of view but also offers many possibilities in medicine such as early detection of diseases and the development of new vaccines and drugs. DNA fingerprint detection from individuals has become a standard-technique in criminology. With these many applications, DNA sequencing, i.e. determining the nucleotide order in a DNA strand, has become a big market for equipment manufacturers as well as service providers.

The chain termination method (developed by F. Sanger) is the state-of-the-art technique for DNA sequencing. Recently two new techniques, "pyrosequencing" and "454 Sequencing" (from the company 454) have been introduced. Despite major differences in sample preparation and detection (chain termination uses electrophoresis for DNA fragment separation and dye or radioactive labels, whereas pyrosequencing and 454 Sequencing are based on chemiluminiscent enzymatic reactions when a nucleotide is incorporated into the DNA strand during replication), all techniques rely on the amplification of the initial amount of DNA by polymerase chain reaction (PCR). Moreover, they also use PCR in the sequencing process itself.

Therefore, chain termination, pyrosequencing and 454 sequencing are all affected by the limitations of PCR (e.g. primer annealed to a second site, RNA contamination acting as primer, reading problems associated with the secondary structure of DNA). Due to these and other constraints, sequencing machines based on the chain termination method can detect a maximum of about 1000 nucleotides, and 454 sequencing can detect only around 100 nucleotides. This has serious disadvantages for whole genome assembly especially for highly repetitive genomes, when genome assembly is ambiguous. PCR is also a rather slow process due to cycling steps at specific temperatures and requires large amounts of (expensive) chemicals.

Alternative sequencing techniques are heavily investigated at universities and in the industry, aiming to not rely on PCR. However, none of them has produced good results so far.

Nanopore sequencing is one of the most favored new techniques, for example as described in US20050102721(A1) and US20030104428(A1).

A DNA molecule is 'pulled' through a thin pore with a diameter in the order of a few nanometer by electrophoresis (in most experiments a solid state pore is used, but also transmembrane proteins in a lipid bilayer have been investigated).

FIG. 1 shows the basic operating principle of conventional nanopore sequencing.

A voltage bias across a membrane causes ions to flow through the nanopore 12 between two ion-containing solutions. By drawing polymers of DNA 14 though the nanopore, the number of ions that pass through is reduced, and this is detected as a change in current.

Ideally, the DNA passes the pore one nucleotide at the time, each nucleotide blocking the current through the pore in a characteristic manner. The sequence of current readings directly represents the DNA sequence. In order to be accurate, the pore diameter must be very small (about the size of a nucleotide) so that a single nucleotide can block the current and it must be sufficiently thin to assure that the signal is modulated by a single nucleotide rather than several.

EP1486775(A1) discloses a nanopore device with two electrodes fabricated at the two sides of the pore. Sequence information is conveyed in the tunnel current between these electrodes as the DNA strand is gradually pulled through the pore. The arrangement is shown in FIG. 2.

Similarly, EP1433744(A1) discloses a nanotube embedded in a substrate with a nanopore processed through the tube and substrate. DNA is sequenced by pulling the strand through the pore and measuring the current between the two parts of the tube when a voltage is applied. The structure is shown in FIG. 3. In this configuration, two voltages are applied—one between the left and right side of the nanotube for obtaining the sequence (e.g. tunnel current across nucleotides), the other in parallel to the pore for pulling the DNA strand through the pore.

Besides considerable difficulties in the manufacturing of these devices (e.g. how to align the pore etch mask to the nanotube in FIG. 3), one of the major shortcomings of the nanopore based sequencing devices presented above is the rather large sensitive area. The spacing between two adjacent bases in a DNA strand is only 0.34 nm. This means the dimensions of the probe used for detecting individual nucleotides must be of the same order or even smaller. However, nanopores with a thickness of less than 1 nm are difficult to produce and many other issues such as material stability, insufficient insulating properties and extremely high capacitance hamper these devices.

As shown in FIG. 2, the electrode distance is typically much larger than the base separation, resulting in a signal that is averaged over all bases in the pore. No single nucleotide detection is then possible. The same applies for the device shown in FIG. 3. Although nanotubes can have rather thin diameters, they never get into the range of the adjacent nucleotide spacing.

With state-of-the-art nanopore based sequencing techniques, a single nucleotide must be repeated around 50 times followed by an at least equally long sequence of another single nucleotide to produce measurable results. The resolution is clearly too low.

According to the invention, there is provided a detector device, comprising:

a substrate;

a source region and a drain region;

a channel region between the source and drain regions;

a nanopore which passes through the channel region, and which connects fluid chambers on opposite sides of the nanopore;

drive means for providing a voltage bias between the fluid chambers;

drive means for providing a voltage between source and drain $V_{SD}$; and a current sensor for sensing a charge flow between the source and drain regions.

The device of the invention uses a nanopore for the confinement of a sample under test (for example nucleotides of a DNA strand) close to a sensor. The size of the sensor can be made similar to the spacing of adjacent nucleotides. In this way, the disadvantages of PCR based techniques are avoided, and single nucleotide resolution can be attained. The device can provide direct contact between the sensor and the sample under test, so that signal disturbance by stray capacitances and resistances are minimized.

In one implementation of the invention, there is provided the integration of a nanopore in the gate area of a structure corresponding to a field-effect-transistor (FET). The conducting inversion layer of such a device has a thickness in the (sub) nanometer range which makes it an ideal sensor for sequencing nucleotides which are only separated by 0.34 nm in a DNA strand.

In another implementation, there is provided the integration of a nanopore in the dot region of a quantum tunneling transistor.

The substrate can have a locally thinner region in the vicinity of the nanopore, to facilitate the drawing of the sample through the nanopore. The locally thinner region can have a thickness of less than 200 nm, more preferably less than 100 nm.

The nanopore preferably has a diameter of less than 10 nm, more preferably less than 5 nm.

Each fluid chamber preferably contains an electrolyte, and the drive means draws the electrolyte across the nanopore. In one example, the electrolyte of the fluid chamber on the channel side of the substrate contacts the insulator layer. In this case, the device has a transistor type configuration, but without the gate contact.

A control electrode can however be provided on top of the channel, with the nanopore extending through the control electrode, and the electrolyte of the fluid chamber on the channel side of the substrate contacting a further insulator layer which is on top of the control electrode. This control electrode operates as a transistor gate electrode, and allows the operating point of the device to be defined independently of the potentials applied to the electrolyte.

Second drive means can be provided for defining a source and/or drain voltage relative to the voltages applied to the fluid chambers. This allows control of the device operating point as well as the control of the flow through the nanopore.

In one example, the channel region surrounds the nanopore. A source-drain current can thus flow around the nanopore, and the sample in the nanopore functions to modulate this current.

Alternatively, the nanopore can extend fully across the channel region. In this case, the device functions as a quantum tunneling device through the sample in the nanopore.

The device may further comprise means for applying a varying electromagnetic field across the nanopore controlled by an excitation current. This provides a further mechanism which can be modulated by the sample in the nanopore.

The device can be manufactured using a substrate which is silicon, silicon on insulator substrate (a silicon layer on a buried oxide layer), a silicon/germanium, GaAs/AlGaAs or other heterostructure or a pnp (or npn) stack with the channel defined as a partially depleted n (or p) region in the middle of the stack.

The invention also provides a method of fabricating a detector device, comprising:
 forming a source region and a drain region on a substrate, with a channel region between the source and drain regions;
 defining a nanopore through the channel region and which connects opposite sides of the nanopore;
 forming fluid chambers on opposite sides of the nanopore and filling them with electrolyte;
 connecting drive means to the fluid chambers;
 connecting drive means to the source and drain regions; and
 providing a current sensor for sensing a charge flow between the source and drain regions.

The invention also provides a method for detecting DNA nucleotide monomers using a device which comprises a substrate, a source region and a drain region, a channel region between the source and drain regions and a nanopore passing through the channel region,
 wherein the method comprises providing a voltage bias between fluid chambers on opposite sides of the nanopore thereby drawing a sample under test through the nanopore;
 providing a voltage bias between source and drain regions;
 sensing a charge flow between the source and drain regions; and
 determining from the sensed charge flow the monomer type.

The charge flow can comprise a modulated field effect transistor source-drain current and/or a tunneling current.

More generally, the invention provides a method for obtaining sequence information of biopolymers by moving them perpendicularly through a thin conductive layer of less than 1 nm thickness, and measuring currents which are modulated by individual nucleotides in close proximity to the layer in a characteristic manner, and deriving sequence information from the current measurements.

The thin conductive layer can be formed by an inversion layer in a conductive substrate, by the two dimensional electron gas of a heterostructure of semiconductors such as Se/Ge or GaAs/AlGaAs, or by partially depleting the p or n type conducting layer in a npn or pnp structure by reverse biasing the pn or np junctions.

The invention will now be described in detail with reference to the accompanying drawings, in which:

FIGS. 7a to 7d shows additional embodiments of the invention;

The invention incorporates a nanopore into the structure corresponding to the gate of a transistor, for example a field effect transistor or a quantum well transistor device.

Figure 1:
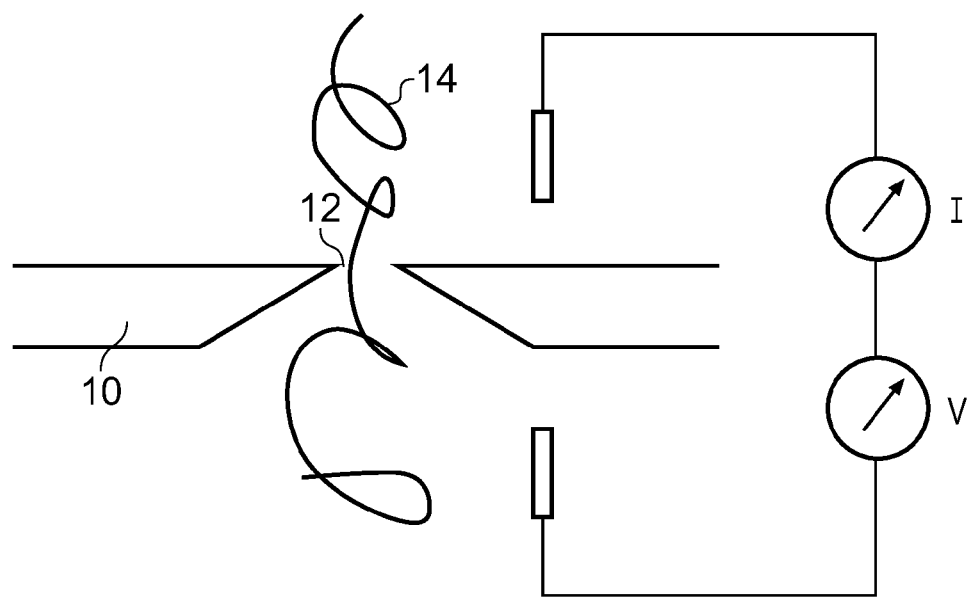
FIG. 1 shows in simplified form a known nanopore detector.
Figure 2:
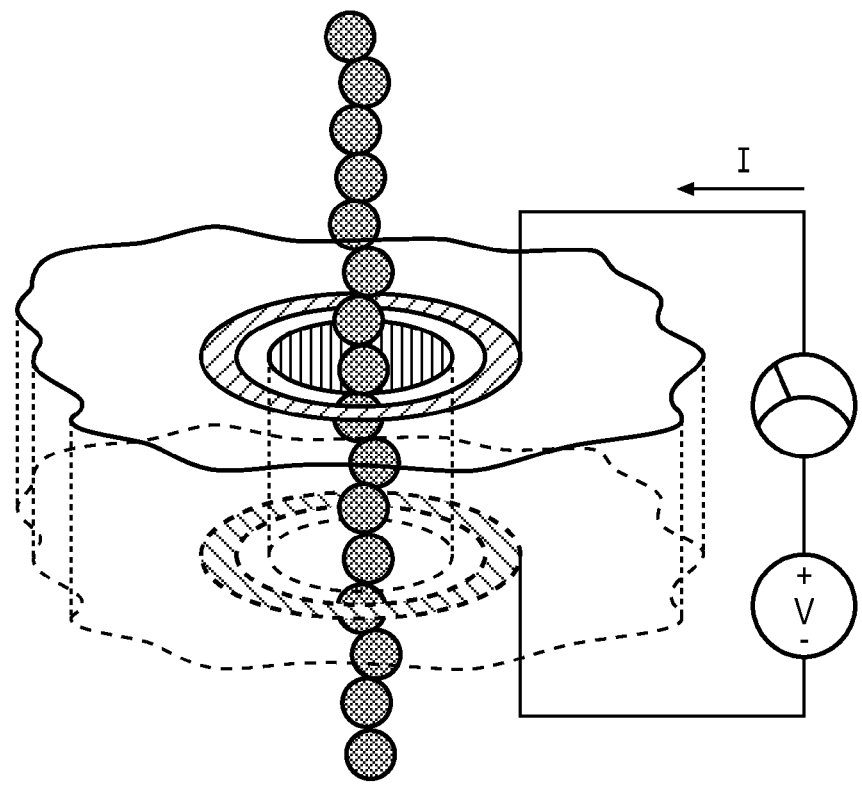
FIG. 2 shows the configuration of a known type of nanopore detector.
Figure 3:
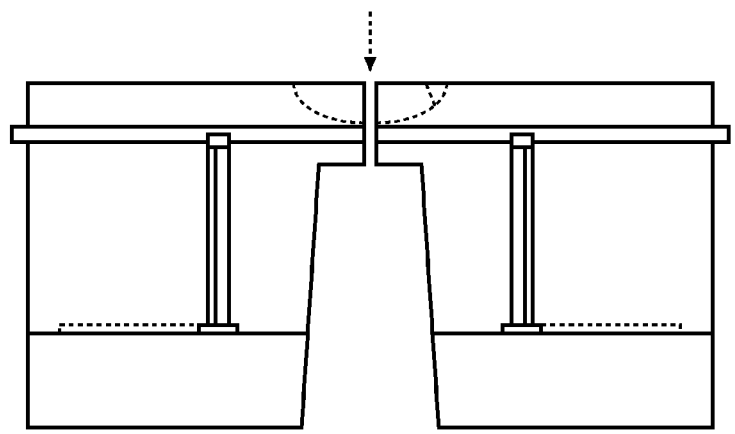
FIG. 3 shows the configuration of another known type of nanopore detector.
Figure 4:
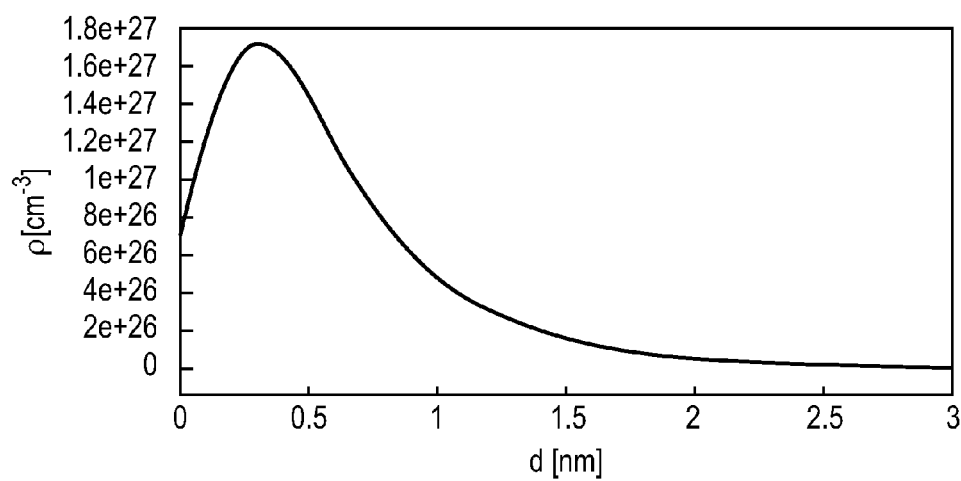
FIG. 4 shows the charge density plot for an inversion channel.

The conducting inversion layer of a FET transistor has a thickness in the (sub) nanometer range, which makes it the ideal sensor for sequencing nucleotides which are only separated by 0.34 nm in a DNA strand. FIG. 4 shows the charge density plot for an inversion channel. In FIG. 4, d denotes the distance in nm from the silicon/oxide interface. The width of the peak at half maximum is clearly below 1 nm.

Figure 5A:
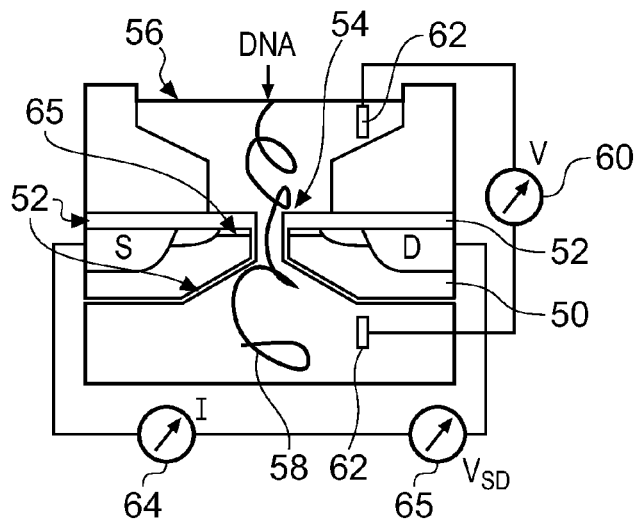
FIGS. 5a to 5f shows first examples of device of the invention.
Figure 5B:
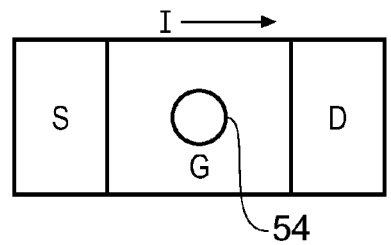

FIG. 5a shows the operating principle of a first example of nanopore FET for DNA sequencing, of the invention. A top view is shown in FIG. 5b, with source (S) drain (D) and gate (G) indicated, and the position of the nanopore 54.

As shown in FIG. 5a, the device of the invention corresponds to a field effect transistor having a substrate 50 with source and drain regions S,D, and an overlying gate oxide layer 52. In the following description, the structure is referred to as a transistor, because it has a number of features in common with a transistor, but has a different gate design, as (in some examples) there is no patterned gate electrode. The use of the term "transistor" should be understood accordingly. The structure can, however, be manufactured with minor modification or additional steps to conventional transistor manufacturing processes.

The channel area of the transistor extends between the source and drain, and is provided with a nanopore 54. The nanopore couples upper and lower chambers 56,58 which contain electrolyte. The nanopore has a diameter only slightly larger than the size of the nucleotides (i.e. smaller than 5 nm).

The gate voltage of the transistor is provided by the electrolyte voltage of the upper chamber, rather than by a patterned gate electrode. Other than this, the structure of the transistor is conventional, and many different FET designs can be used.

A voltage bias is provided between the fluid chambers by a voltage source 60 associated with electrodes 62, and a current sensor 64 enables sensing of the source-drain current of the transistor. A further voltage source 65 ($V_{SD}$) also provides a source drain voltage. A further voltage source may be used for controlling the bulk voltage (not shown).

The DNA is moved through the nanopore 54 by applying a voltage between the top and bottom chambers of the cell. This voltage also acts as the gate voltage and sets the working point of the transistor. The nucleotides passing the nanopore modulate the source-drain current if they are in close proximity to the channel.

With this design, the resolution and sensitivity can be so high that individual nucleotides can be detected.

Since the sensitive area of the detector (in vertical direction) is limited to the thickness of the inversion layer, the nanopore can be much longer than in the conventional nanopore devices described above. The sequencing is based on modulation of the source-drain current not by measuring the current through the pore (although synchronous measurement of both currents may be useful for voltage control and feedback).

In principle two effects can contribute to the modulation of the source-drain current:

Nucleotides with different charges can modulate the gate voltage. Many experimental and theoretical studies have been done on the electron affinity of DNA nucleotides. The electron affinity is the amount of energy required to add an electron to a neutral atom in the gas phase to form an ion. The concept also applies to molecules and gives information about their behavior in solution. Although a large range of different values derived from theoretical simulations is reported, in most studies they follow a common trend with A<G<<C<T i.e. adenine has the lowest electron affinity, thymine the highest.

Atoms/molecules with a low electron affinity value tend to be negatively charged in solution while those with a high electron affinity are positively charged (e.g. Na −53 kJ/mol (positively charged in solution), Cl −349 kJ/mol (negatively charged in solution)). Based on the different electron affinities, it can be assumed that the nucleotides form differently charged ions in aqueous solutions. These different charges in the DNA strand may influence the conducting channel when they are close to the inversion layer thus modulating the source-drain current which in return yields information on the nucleotide sequence. Measuring single charges is rather difficult, especially at room temperature but recent publications have shown that this is possible e.g. if the transistor is operated in the sub-threshold regime.

Tunneling across the nucleotides. Due to their different electron affinity and morphology etc., the tunnel current from source across the nucleotide to drain may be specific for each nucleotide thus revealing the sequence of DNA strands. Tunneling may particularly play a role in devices with very narrow channels where almost the entire channel is obstructed by the pore.

If the channel is so narrow that it is completely obstructed by the pore, the device could operate similarly to a single electron transistor, with source and drain being the contacts, the thin oxide layer in the pore being the barrier and the individual nucleotides representing the 'island' that is charged/discharged.

The discussion above relates to single stranded DNA. In double stranded DNA, each nucleotide of the first strand is connected to its complimentary nucleotide of the second strand (i.e. A to T, and G to C), thus the signal that is measured by the perpendicular gate current (channel modulation or tunneling) yields the combined properties of the pair rather than the individual nucleotides. When sequencing double-stranded DNA, it is possible only to discriminate the two pairs not the individual nucleotides.

The key differentiating features of the system of the invention with respect to previous approaches are:

The nanopore is located in the channel of a FET or the island of a single electron transistor.

There is direct modulation of the source-drain current, with no additional conductors and no additional stray capacitances.

Several factors can affect the source-drain current: channel modulation by charged nucleotides, tunneling across nucleotides, nucleotides being part of or acting as the island of a single electron transistor.

Figure 5C:
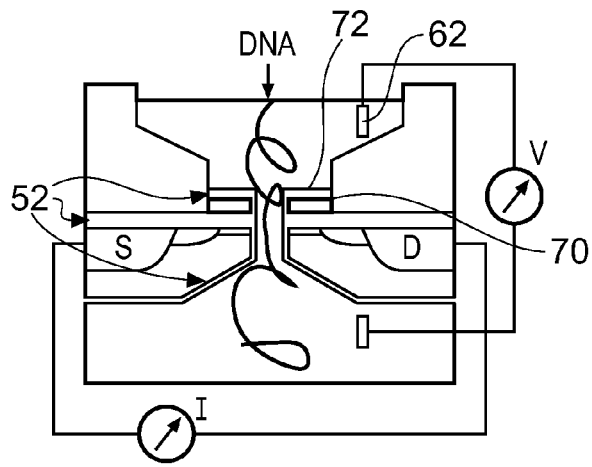

FIG. 5c shows a second embodiment of the invention, in which an additional control gate 70 is provided.

This configuration offers control over the gate voltage independently of the voltage applied between the top and bottom chambers. In order to avoid electrochemical reactions if the voltage between control gate and top electrolyte gets too large, the control gate is insulated by a dielectric 72 from the electrolyte, and this is achieved by not completely removing the passivation or inter-metal dielectric layers on top of the control gate. Alternatively the insulating dielectric can be deposited (e.g. PVD, CVD) or grown by electrochemical oxidization of the control gate material. An oxideless configuration incorporating a metal control gate without gate dielectric (similar to a junction FET (JFET)) is also possible. In principle, the insulation layer on top of the control gate can be omitted. Theoretically, the deposition/growth of the gate dielectric 52 in FIG. 5a is also not necessary and the gate can be contacted directly by the electrolyte (a thin chemical oxide forms automatically).

Figure 5D:
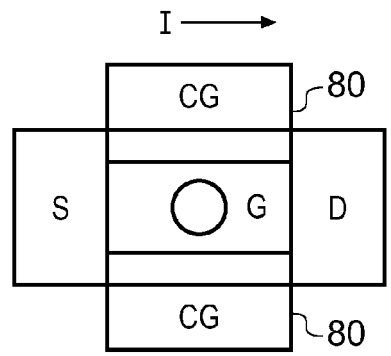

FIG. 5d shows the top view of a similar device but with two separate control gates 80 (CG). In this configuration, a substantial part of the gate is contacted by electrolyte (e.g. water) while its outer rims are covered by the two control gates. Depending on the voltages applied between electrolyte and the control gates, the actual channel width can be considerably smaller than the nominal channel width defined by the width of the source-drain contacts (suppression of the inversion channel beneath and near the regions covered by the control gates). This allows much narrower channels than can be made using current technology, and concentrates current flow near the pore region. This increases its relative influence on the overall current. In the most extreme case, the remaining channel is as narrow as the pore i.e. the current must fully flow (tunnel) across the nucleotides. This makes the device similar to a single electron transistor, with the nucleotides playing the role of the island and the oxide at the pore walls being the barrier.

The gate area may again be controlled by an additional (metal) gate processed on top (in-between the two control gates) that is insulated from the electrolyte and the adjacent control gates. Such a configuration allows maximum control over the channel width and inversion layer independent of the electrolyte voltage (not shown).

Figure 5E:
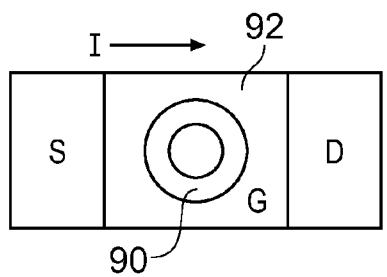

FIG. 5e shows another embodiment of such a single-electron nanopore FET, with the island 90 and narrow surrounding 'gate' area 92.

The pore is etched right through the center of the island 90 forming the single-electron-transistor. The barrier of the single electron transistor insulating the island from the channel may be formed by different doping of the island versus the surrounding 'gate' area 92, allowing depletion in the island region while it is surrounded by a zone ('main' gate area) with inversion layer, or vice versa. Alternatively, the barrier is simply formed by the oxide layers in the pore. Again, the device can be implemented with or without control gate (in this configuration the control gate would be on top of the 'gate' area 92 and the the island in contact with the electrolyte).

Figure 5F:
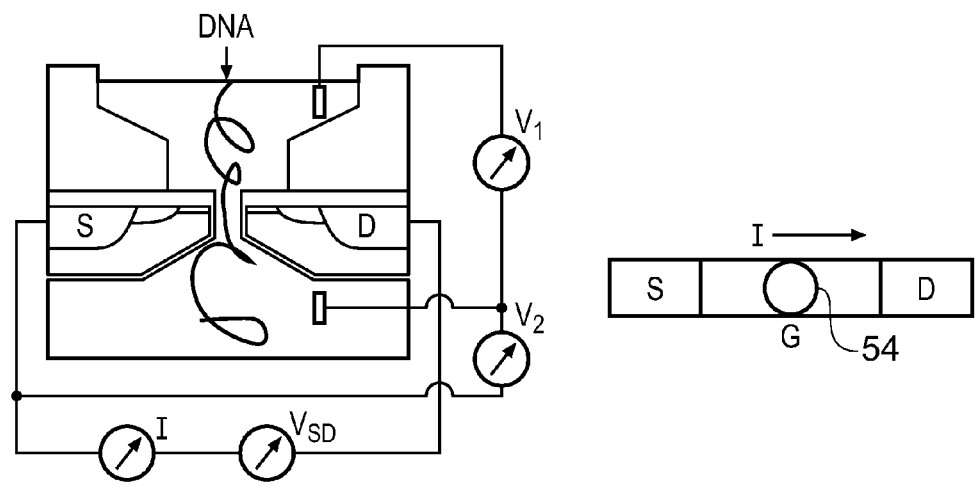

FIG. 5f shows a further embodiment again using tunneling across the junction between the source and drain realized by an extremely narrow channel.

In this example, the pore completely blocks the conductive channel.

The operating principle of such a tunneling device will be explained below.

Figure 6A:
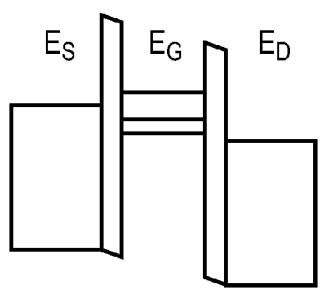
FIGS. 6a to 6b show examples of the energy diagrams in the devices and sample

The voltages V1 and V2 together define the gate voltage that defines the discrete energetic levels (represented by $E_G$) of the DNA nucleotide in the nanopore with respect to the Fermi energy levels $E_S$ and $E_D$ in the source and drain regions respectively, see the energy diagram in FIG. 6a. $E_G$ can be moved with respect to $E_S$ and $E_D$ by changing V1 and/or V2.

A single nucleotide located in the pore at the height of the conductive channel acts as the 'island' of a single electron transistor, as outlined above. If the energy states of source, nucleotide and drain are correctly aligned, i.e. $E_S \geq E_G$ (i.e. one of the free states there)$\geq E_D$ then resonant tunneling occurs, so that electrons can tunnel from the source across the barrier (which is e.g. the thin oxide layer on the pore wall) onto the nucleotide and from there to the drain.

Figure 6B:
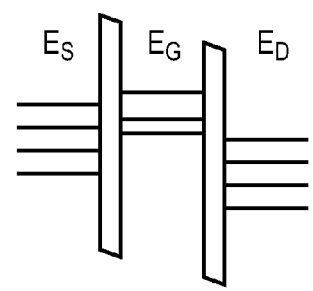
Figure 8A:
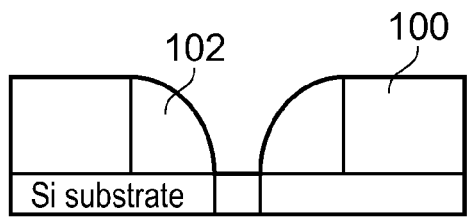
FIGS. 8a and 8b show how the nanopore may be formed.
Figure 8B:
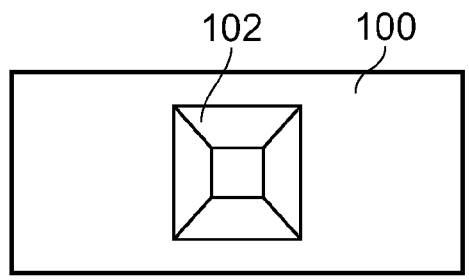

FIG. 6b is an energy diagram which also shows discrete energy levels in the conductive channel.

This arrangement has at least 3 voltage sources; V1, V2 and $V_{SD}$, and another voltage source can be used to control the bulk voltage (not shown).

Different energy states of a nucleotide (represented by the different lines at $E_G$ in FIG. 6a) can contribute to resonant tunneling yielding a specific relation between the current and e.g. the value of V2 (also dependent on $V_{SD}$).

This measurement principle is essentially tunneling spectroscopy. Since the four nucleotides have different energy states, the current-voltage relationship is specific for the individual nucleotides. As the DNA strand is pulled through the pore, the current-voltage characteristic is modulated according to the respective nucleotides passing the conductive channel yielding specific sequence information.

The different examples above show that measurement of transistor currents at fixed voltages (source, drain and gate) can be used or tunnel spectroscopy can be used. By measuring the tunnel currents at different 'gate' voltages (e.g. modulate the bath voltage V2 with respect to the voltage in the device, i.e. shift $E_G$ with respect to $E_S$ and $E_D$ in the energy diagram) more data about the nucleotide in contact with the sensor can be obtained allowing easier and more reliable discrimination between the 4 nucleotides.

The configuration of a pore, coated with thin dielectric layer, with a nucleotide contacted by an inversion layer from either side is similar in effect to a quantum dot or the island of a single-electron transistor. It is a confined system of electrons (here the nucleotide) coupled via tunnel barriers (here the oxide liner of the pore) to macroscopic electrodes (here the inversion layer in contact with source and drain) across which electrons can tunnel in and out of the confined volume. Two processes affect the tunnel current: the addition of electrons to the dot and the excitation of electrons on the dot to higher energy states. The first is governed by the capacitance of the dot and its Coulomb charging. If an electron is added to the dot, its energy increases roughly by $e^2/C$ (C is the capacitance of the dot) causing a blockade in current if the energy in the dot is raised above the potentials of the electrodes. In order for Coulomb blockade effects to be visible at room temperature (thermal energy $k_B T = 25$ mV) the dot capacitance must be sufficiently small ($e^2/C > k_B T$), which is the case for the system proposed.

The second process involves the excitation of electrons within the system yielding an excitation spectrum that is specific to the energy states and therefore to the nucleotide (separation of the energy states in the nucleotides is frequently larger than the thermal energy thus they should be distinguishable at room temperature). In the energy diagram of FIG. 6a, excitation means that an electron is excited from one energy level (line) to a higher energy level (line above)

Transport through quantum dots can also be affected by an external magnetic field. A variety of effects is observed that are based on the addition as well as excitation of electrons. These effects are expected to be different for different nucleotides, providing an additional way to obtain sequence information. In this case, the nanopore is placed in a (time dependent) magnetic field, e.g. between two Helmholtz coils that are connected to an AC current source. Tunnel currents are measured with respect to the magnetic field and the applied voltages.

The key element in the detection principles and devices above is the thin conductive layer with a thickness in the range or smaller than the separation between two adjacent nucleotides in a DNA strand. So far the transistor channel or the 'electrodes' of the tunnel devices are formed by an inversion layer in a semiconducting substrate. Alternatively a two dimensional electron gas (2DEG) that forms at a heterostructure, for example Si/Ge or GaAs/AlGaAs, can be used as conductive sensor layer. An advantage as compared to the inversion layer is that the 2DEG already exists without applying a gate voltage, thus allowing more freedom in setting V1 and V2. Since the 2DEG is at the interface of the two materials and thus remote from the dielectric insulator, the noise is much lower as there is less influence from the trapping/release of charges from interface states at the semiconductor/dielectric interface or other traps in the dielectric.

Moreover, the confinement to the interfacial region results in discrete energy levels in the channel (see FIG. 6b) which may provide increased sensitivity to the device. Discrete energy levels can also be obtained with inversion layers in Si if the Si bulk material is thin enough e.g. <20 nm, as this provides confinement in the z-direction with splitting of the energy bands into discrete states (lines in FIG. 6b). Such layers can be achieved by thinning down the top silicon layer with SOI (silicon-on-insulator) wafers.

A thin conductive layer can also be formed by depleting a highly doped layer from the top and bottom e.g. a pnp structure where both pn junctions are reverse biased such that the n-conducting layer is almost fully depleted except for a thin channel remaining in its middle.

FIG. 7 shows various embodiments of the invention that have been outlined above.

FIG. 7a shows a thin Si layer fabricated using a SOI wafer. The thin silicon layer is shown as 90, on a buried oxide layer. If the layer is very thin, the energy states in the source and drain channel become discrete because of the vertical confinement.

In FIG. 7b, a Si/Ge heterostructure is shown, with the conductive layer (channel, 2DEG) formed at the interface between both materials. This structure also gives discrete energy levels in the source and drain regions.

In FIG. 7c, the channel is formed in a partially depleted n-Si layer of a pnp stack. Both pn junctions (formed between the bottom p-layer and n-layer in the middle and top p-layer and the n-layer in the middle) are reverse biased depleting most of the n layer leaving only a thin conductive channel in the middle.

FIG. 7d shows coils 92 to induce a magnetic field to the device of the type shown in FIG. 6a. Tunnel currents are then measured with respect to the phase and amplitude of the excitation current (optionally a separate device can be used to correlate the phase between the excitation current Ierr, the applied voltages and the measured current I; not shown).

The external electromagnetic field modulates the electronic states of the nucleotides (and sensor channel), and this influences the source drain current. Since the magnetic field may have different effects on the energy states of the different nucleotides this provides an alternative/additional means of reading the sequence.

Most steps for the implementation/manufacturing of the devices above are straightforward. Except for the final steps, they are essentially identical to a state-of-the-art CMOS process (e.g. C065).

In the most basic device shown in FIG. 5a these additional processing steps are to provide a reduced thickness of the stack through which the pore passes and the formation of the nanopore itself. These steps are described below with reference to FIG. 10 (not drawn to scale). Note that only the essential steps are shown, standard procedures such as resist deposition lithography etc. are omitted for clarity.

Figure 10A:
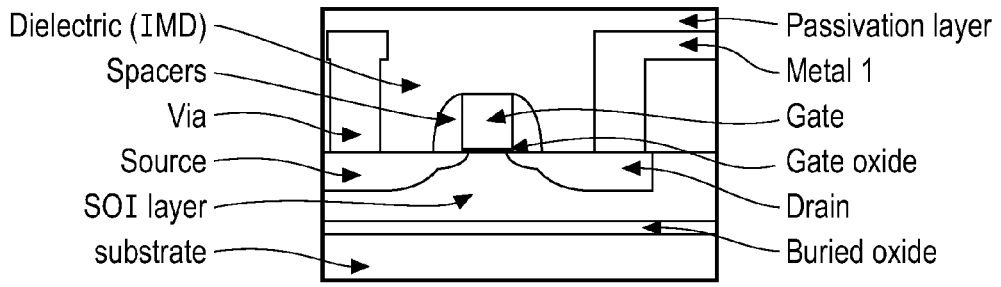
FIGS. 10a to 10g shows an example process flow describing the manufacturing of a nanopore device.
Figure 10B:
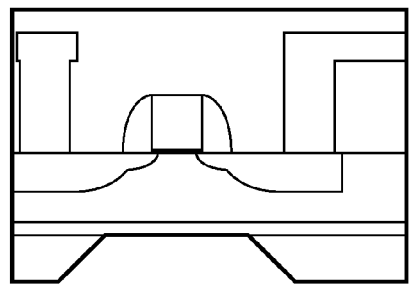
Figure 10C:
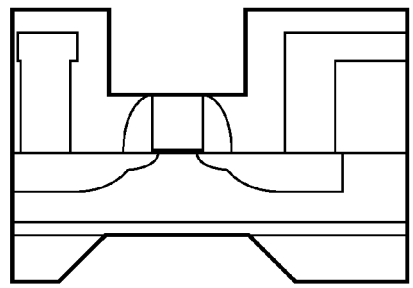

The starting point is a device/wafer that underwent a full 'conventional' process flow including passivation layer deposition and bondpad patterning; such a device is shown in FIG. 10a with all relevant components indicated (several components e.g. the inter metal dielectric (IMD) may consist of several layers of different materials; not shown in detail). The backside of the wafer is locally thinned/etched beneath the channel region 65 such that only a thin layer of Si substrate (e.g. less than 100 nm thickness) remains underneath the gate oxide. The thinner the stack i.e. the shorter the pore, the easier it is to pull the DNA through. The resulting taper is shown e.g. in FIG. 5a. This step can easily be done if the device is processed on silicon-on-insulator wafers. In this case the buried oxide layer can serve as etch stop during the etch of the bulk wafer see FIG. 10b.

Figure 10D:
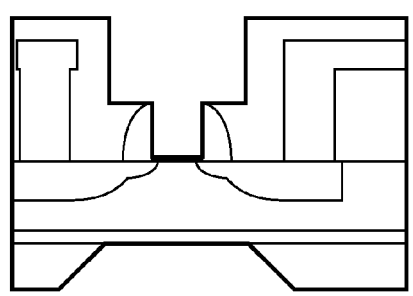
Figure 10E:
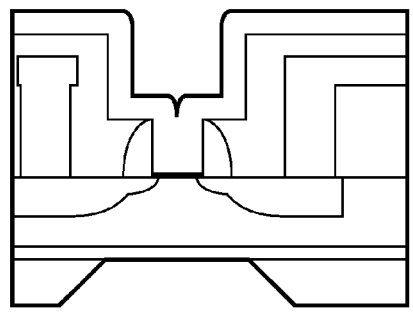

The passivation layer in the gate region is then locally removed from the top side (by etching) (FIG. 10c) followed by etching away the gate stack (FIG. 10d). If needed the gate oxide can be removed and another gate dielectric can be deposited. The final steps comprise etching of the pore e.g. according to the scheme presented in FIG. 10e to 10g and attachment of the electrolyte chambers.

Etching of small pores with diameters of less than 10 nm and very high aspect ratios above ten is a major challenge in the manufacturing of these devices. While such small structures can be written with e-beam lithography they are difficult to implement with standard CMOS process technology.

Figure 10F:
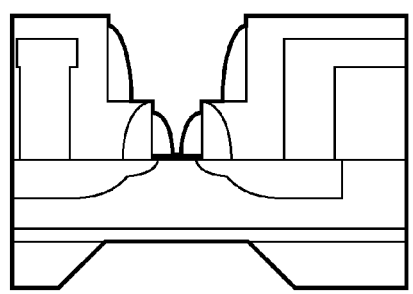
Figure 10G:
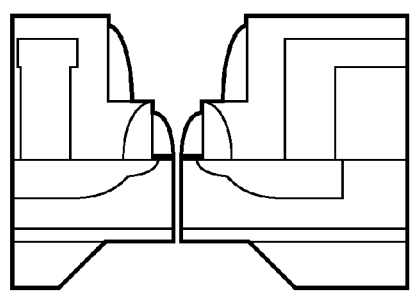

FIG. 8 and FIGS. 10e to 10g show how small pores can be obtained with conventional lithography. First, a small opening/cavity (e.g. quadratic or circular) is etched into a hardmask 100 e.g. oxide or nitride layer. In FIG. 10d this opening is defined by the hole remaining after the etch of the gate stack. With state-of-the-art optical lithography equipment feature sizes in the range of 50 nm can be reached for such a hole. The aperture of this hole is further reduced by spacers 102, a standard process module in the production of MOS transistors. The process involves the following steps: uniform deposition of an e.g. oxide or nitride layer across the hole and the surrounding areas (FIG. 10e), followed by anisotropic etching until a small aperture opens at the bottom (FIG. 10f). This aperture serves as a mask for the subsequent etching of the pore with sub-10 nm diameter (FIG. 10f), In the selection of materials, care must be taken that enough etch selectivity is provided between the mask and the materials to be etched.

Alternatively, the pore can be 'drilled' with a focused ion beam or prepared with methods known from the manufacturing of conventional nanopores (e.g. ion/electron-beam sculpturing). If silicon on insulator wafers are used, the final thickness of the stack through which the pore passes (i.e. the length of the pore) is given by the thickness of the buried oxide (minus the oxide removed during the etching of the bulk substrate), the thickness of the silicon on insulator layer and the gate oxide thickness. Preferentially the overall thickness is less than 200 nm.

The blank silicon surfaces in the pore rapidly oxidize in the aqueous environment of the electrolyte forming a thin 'gate' oxide along the pore walls. This is shown in FIG. 5a, with reference 52 showing the different oxide layers.

If needed, the thickness of these insulation layers can be increased by local oxidation e.g. by heating with a laser beam or by strong oxidation solutions. Moreover additional dielectrics (oxide, nitride) can be deposited on the top and bottom on either side of the pore. Electrochemical processes or ALD (atomic layer deposition) may also be used.

Processing of devices with control gate as shown in FIG. 5c is very similar. Instead of etching the gate stack away as described above, the pore 54 is etched right through the gate and the channel beneath. (In this case the cavity and spacers defining the etch mask for the pore are processed in the IMD above the gate). The aspect ratio (length to diameter) of the pore is however larger (due to the additional layer added by the gate) so that it is more difficult to etch.

Devices with two control gates (FIG. 5d) can be processed by etching a slit into the gate stack that fully separates the two parts followed by deposition of a thin insulating layer and etching the pore. An additional metal contact for controlling the channel (independent of the electrolyte voltage) can be deposited after etching the slit into the gatestack, e.g. with e-beam lithography and lift-off (subsequent steps are then the same as before).

Devices as in FIG. 7a are processed in the same way, only that SOI substrates are used. Optionally, the top Si layer of the SOI (silicon on insulator) substrate can be thinned down to less than e.g. 20 nm at the beginning of the conventional CMOS process. This yields discrete energy levels in the source and drain region as shown in FIG. 6b. Similarly, devices with hetrostructures are made by first depositing the heterostructure (e.g. Ge on a bulk Si or SOI substrate or GaAS and AlGaAs on a suitable substrate) and processing the transistors similar to conventional CMOS processing. The final steps for substrate thinning and pore etch are the same as described above. The same applies for FIG. 7c where a highly n-doped Si layer is deposited onto a p-substrate (e.g. by epitaxy) followed by deposition of another p-doped layer on top. Source and drain contacts are established with the n-layer the p-layers are contacted to reverse bias the pn junctions and obtain the narrow channel.

The detailed processes required will be apparent to those skilled in the art, and outline descriptions of the processes have been given. Some embodiments may not need all steps of a standard CMOS flow e.g. with the heterostructure device the extension implant is not needed. There are many other ways to produce the devices which will be routine to those skilled in the art.

The description above is limited to features and processes for MOSFETs. However, the dielectric layer of these devices with its large number of surface and interface charges and traps cause considerable noise which may prevent the detection of the weak signals from the nucleotides. In order to minimize this noise, JFETs can be used. The gate is then directly contacted by a metal thus avoiding any oxides and their specific problems. Again the metal can be contacted and controlled by the electrolyte or a separate (gate) contact.

Figure 9C:
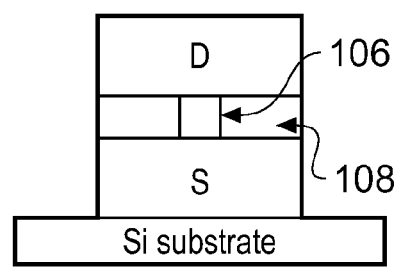
FIGS. 9a and 9b show a fourth example of device of the invention.
Figure 9D:
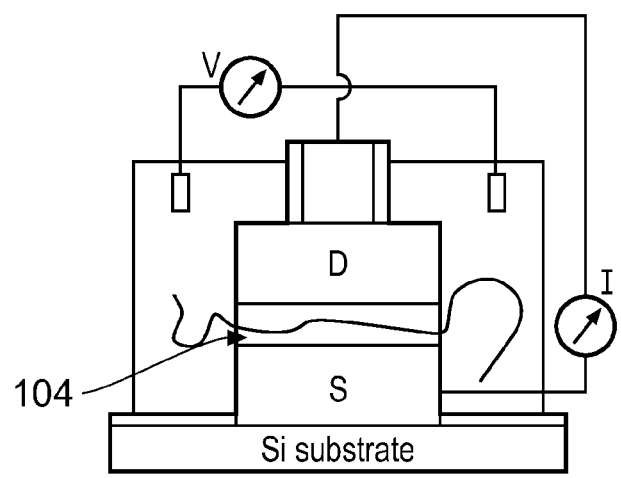

FIG. 9 shows an alternative sequencing device featuring a horizontal nanopore embedded in a FinFET-like structure. The pore is formed by selective etching of a small SiGe bar surrounded by epitaxially grown Si.

The operating principle is essentially the same as in the devices above. Unlike conventional FinFETs the source is located at the bottom and the drain on top with a vertical current flow. As in the device shown in FIG. 5a, the 'gate voltage' is controlled by the voltage in the electrolyte creating an inversion channel 104 at one side of the structure. Voltages must be set such that a channel forms only at one side of the pore. This makes it possible to discriminate the contribution of either side, making the detection of individual nucleotides that enter and leave the pore possible. DNA Nucleotides passing by the channel modulate the source-drain current and allow detection of the DNA sequence.

Manufacturing of the device of FIG. 9 is also straightforward, in principle. First, a sacrificial material, e.g. SiGe, is deposited on a bare Si wafer (doped to form the source) and etched to a long bar with a small cross section 106 FIG. 9a lying on the substrate, or into a long cylinder with sub-10 nm diameter. Next the channel material (lowly doped Si) is deposited (108 in FIG. 9a, for example by epitaxial growth, and planarized (optional) followed by epitaxial growth of the drain region.

A fin-like structure is then etched from this stack and the sacrificial material is removed (SiGe can be etched with high selectivity to Si) leaving a small pore in the center of the device. The overall length of the device is in the range of 100 nm or below. The Si surfaces are again passivated by a thin oxide layer.

The drain is contacted from the top as shown in FIG. 9b with a contact that is electrically insulated and that separates the electrolyte in a left and right compartment.

The entire device may further be integrated into a microfluidic system for transporting the DNA.

A voltage is applied between the left and right compartment that pulls the DNA through the pore and sets the gate voltage. The source-drain current then reveals the sequence information.

The invention is of particular interest for sequencing of DNA and other (bio) polymers or proteins. Although only single pores have been discussed above, CMOS process technology allows the manufacturing of large arrays of nanopore FETs enabling massive parallel sequencing at high speed. Moreover signal conditioning circuits such as amplifiers, filters and ADCs (analog to digital converter) may be implemented on the same chip/die in close proximity to the sensor device. This prevents signal loss e.g. in the otherwise long connection lines to external amplifiers and can be essential for the detection of the small signals with a sufficient signal-to-noise ratio. Such circuits may be crucial for the detection of individual nucleotides and sequencing of DNA.

In order to obtain a good I-$V_{SD}$ spectrum, each nucleotide should remain in contact with the 'sensor' to allow signal averaging to reduce noise or, in case of tunnel spectroscopy, to allow the current spectrum to be measured in a certain voltage ($E_G$) range. The 'residence' time of each nucleotide at the sensor can be increased/controlled by modulating $V_1$ for example using a square wave or saw tooth voltage, and superposing these on a DC voltage. A feedback loop can be used to control the movement of nucleotides through the pore according to the current measurements.

The device of the invention can have fluid chambers which are part of a micro fluidic system transporting the DNA and electrolyte to the detector device. Signal conditioning circuits can also be provided, such as amplifiers, filters and ADCs (analog to digital converters) on the same chip. These signal conditioning circuits can be used to improve the Signal-to-Noise ratio of the detected signals. A device can incorporate several of the individual detector devices on a single chip/die.

The invention also provides the method for creating an etch mask for nanopores comprising the isotropic deposition of a masking layer onto a larger cavity and subsequent anisotropic etch of this layer until a small opening forms in the center.

Various modifications will be apparent to those skilled in the art.

The invention claimed is:

1. A detector device, comprising:
 a substrate;
 a source region in the substrate and a drain region in the substrate;
 a channel region in the substrate and providing a current path between the source and drain regions;
 a nanopore which passes through the channel region, and which connects first and second fluid chambers on opposite sides of the nanopore;
 a first voltage source configured and arranged to provide a voltage bias between the first and second fluid chambers;
 a control gate located in a layer on the substrate and configured and arranged to provide a gate voltage that controls the current path in the channel region and that is independent of the voltage bias provided between first and second fluid chambers;
 a dielectric layer located on the substrate between the channel region and the control gate;
 a second voltage source configured and arranged to provide a voltage between source and drain; and
 a current sensor for sensing a charge flow between the source and drain regions.

2. A device as claimed in claim 1, wherein the nanopore passes through the substrate.

3. A detector device as claimed in claim 2, wherein the nanopore passes through the dielectric layer and the control gate.

4. A device as claimed in claim 2, wherein the substrate has a locally thinner region in the vicinity of the nanopore.

5. A device as claimed in claim 4, wherein the locally thinner region has a thickness of less than 200 nm.

6. A device as claimed in claim 5, wherein the locally thinner region has a thickness of less than 100 nm.

7. A device as claimed in claim 1, wherein the nanopore has a diameter of less then 10 nm.

8. A device as claimed in claim 7, wherein the nanopore has a diameter of less then 5 nm.

9. A device as claimed in claim 1, wherein each fluid chamber contains an electrolyte.

10. A device as claimed in claim 9, wherein the electrolyte of the fluid chamber on one side of the channel contacts an insulator layer.

11. A device as claimed in claim 8, further comprising an insulator layer which is on top of the control gate, and wherein the nanopore extends through the control gate.

12. A device as claimed in claim 1, wherein the control gate, located in a layer on the substrate, is over the channel region and is between two additional control gates, the two additional control gates being respectively located over opposite edges of the channel region.

13. A device as claimed in claim 1, wherein the second voltage source is configured and arranged to provide a source and/or drain voltage relative to the voltage bias applied to the fluid chambers.

14. A device as claimed in claim 1, wherein the channel region surrounds the nanopore.

15. A device as claimed in claim 1, wherein the nanopore extends fully across the channel region.

16. A device as claimed in claim 1, further comprising a circuit configured and arranged to apply a varying electromagnetic field across the nanopore in response to an excitation current.

17. A device as claimed in claim 1, comprising a silicon substrate.

18. A device as claimed in claim 1, comprising a silicon on insulator substrate, comprising a silicon layer on a buried oxide layer.

19. A device as claimed in claim 1, comprising a silicon/germanium heterostructure.

20. A device as claimed in claim 1, comprising a GaAs/AlGaAs heterostructure.

21. A device as claimed in claim 1, comprising a pnp or npn structure with a conductive sensor channel defined by reverse biasing both pn or np junctions respectively, thus partially depleting the central n or p region.

22. A device as claimed in claim 1, wherein the nanopore extends parallel to the substrate in a FinFET structure.

23. A device as in claim 1, wherein the first voltage source is connected to a first electrode in the first fluid chamber, and is connected to a second electrode in the second fluid chamber, and is configured and arranged to apply a voltage bias between the first and second fluid chambers by applying a voltage to the respective electrodes, to move molecules through the nanopore between the chambers.

24. A device as in claim 1, wherein, the first and second fluid chambers are separated from one another by a portion of the substrate and the channel region, and the nanopore has sidewalls that extend between the respective chambers and on a surface of the channel region.

25. The detector device of claim 1, wherein the control gate is a metal control gate.

26. The detector device of claim 24, wherein the control gate and the first fluid chamber are located on a first side of the nanopore, and the first control gate is insulated from the first fluid chamber by a dielectric layer.

27. The detector device of claim 1, wherein the source, drain, channel region, control gate, and nano-pore form a single electron nanopore FET.

28. A detector device, comprising:
 a substrate;
 a source region in the substrate;
 a drain region in the substrate;
 a channel region providing a controllable current path that is in the substrate and that is between the source and drain regions;
 a nanopore, which passes through the channel region, and which connects first and second fluid chambers on opposite sides of the substrate;
 a first voltage source configured and arranged to provide a voltage bias between first and second electrodes, respectively located in the first and second fluid chambers;
 first and second gates being respectively configured to control the current path using a gate voltage that is independent from the voltage bias provided between the first and second electrodes;
 a dielectric layer located between the first and second gates and the channel region in the substrate;
 a second voltage source configured and arranged to provide a voltage between the source and the drain; and
 a current sensor for sensing a charge flow between the source and drain regions.

* * * * *